United States Patent [19]

Brush

[11] 4,172,448
[45] Oct. 30, 1979

[54] FLUID SAMPLING DEVICE

[75] Inventor: Donald C. Brush, Ballwin, Mo.

[73] Assignee: Sherwood Medical Industries Inc., St. Louis, Mo.

[21] Appl. No.: 818,784

[22] Filed: Jul. 25, 1977

[51] Int. Cl.$^2$ .............................................. A61B 5/10
[52] U.S. Cl. ..................................... 128/766; 128/767
[58] Field of Search ......... 128/2 F, DIG. 5, 218 NV, 128/215

[56] References Cited

U.S. PATENT DOCUMENTS

| | | | |
|---|---|---|---|
| 2,722,257 | 11/1955 | Lockhart | 128/DIG. 5 |
| 2,832,344 | 4/1958 | Davidson | 128/DIG. 5 |
| 2,876,775 | 3/1959 | Barr et al. | 128/DIG. 5 |
| 3,181,529 | 5/1965 | Wilburn | 128/2 F |
| 3,322,114 | 5/1967 | Portnoy et al. | 128/2 F |
| 3,340,869 | 9/1967 | Bane | 128/DIG. 5 |
| 3,867,923 | 2/1975 | West | 128/2 F |

FOREIGN PATENT DOCUMENTS 1469025  2/1967  France .............................. 128/DIG. 5

*Primary Examiner*—John D. Yasko
*Attorney, Agent, or Firm*—Stanley N. Garber; William R. O'Meara

[57] ABSTRACT

A blood sampling device includes an expansible, flexible container which, when unfilled, lies flat with its opposed sides together. The container is connected to a support having a passage for connecting the container with a needle cannula. A manually operable valve is disposed between the passage and the container. A gas vent communicates with the passage and has a hydrophobic filter for allowing air in the needle and passage to escape without entering the collection chamber of the container. The container has an isolation chamber at the proximal end for isolating air or air bubbles that might enter the collection chamber as a result of error in sampling technique. By hand manipulation of the container, such air bubbles can be moved from the collection chamber into the isolation chamber to isolate the air bubbles and prevent further absorption of oxygen from such air bubbles into the blood sample in the collection chamber. A closure cap is provided which substantially avoids the introduction of air into a filled container when employed to close the container.

28 Claims, 8 Drawing Figures

U.S. Patent     Oct. 30, 1979     4,172,448
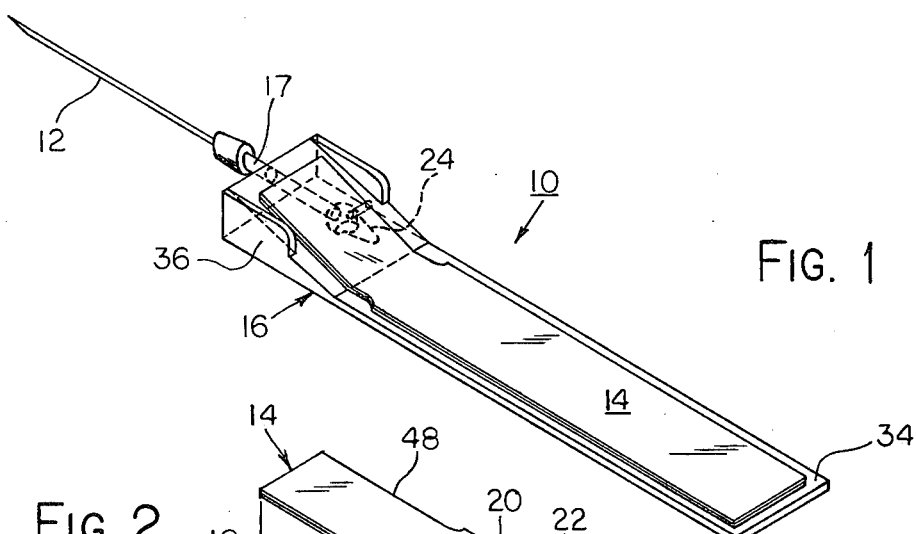
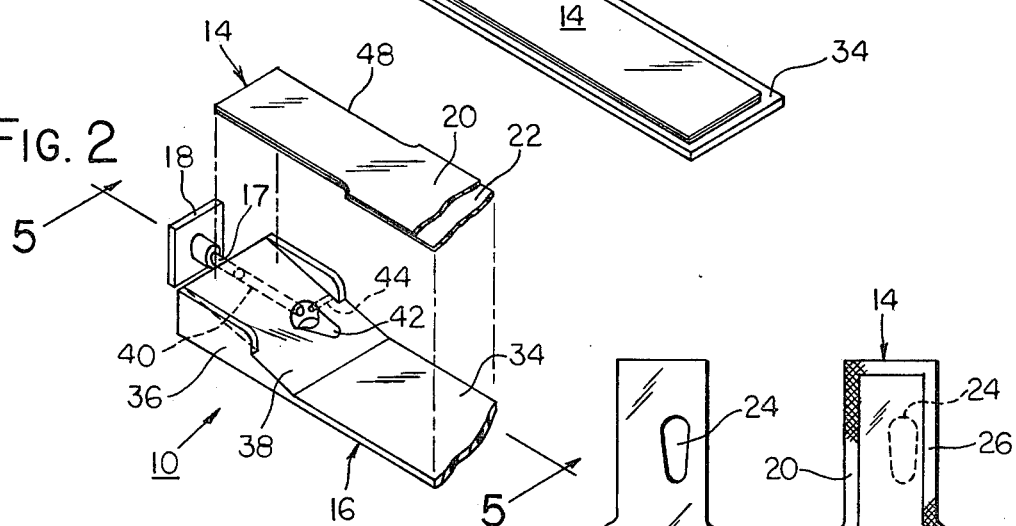
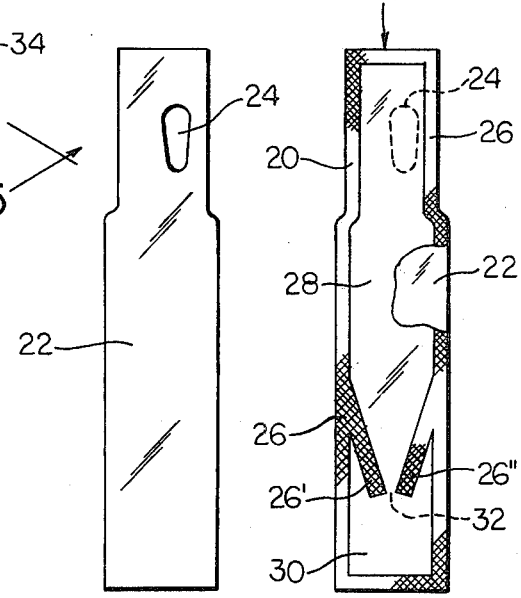
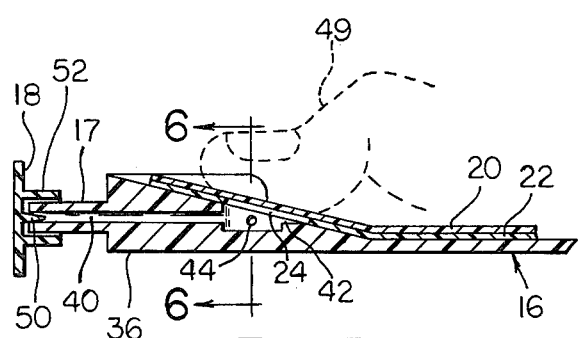
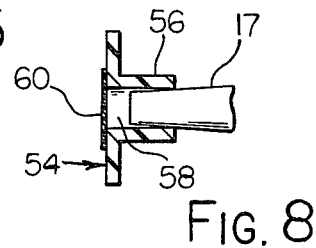
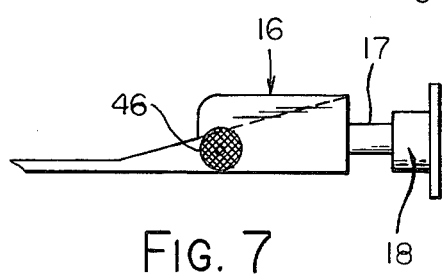
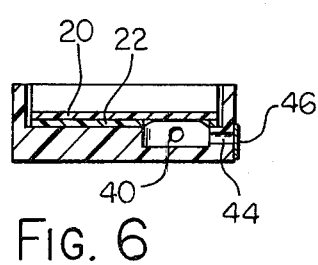

FLUID SAMPLING DEVICE

BACKGROUND OF THE INVENTION

This invention relates to liquid sampling devices and more particularly to blood collection devices used to obtain blood samples for blood-gas analysis.

Blood-gas analysis machines are used in measuring the amounts of gases, such as oxygen and carbon dioxide, in a patient's blood. Blood obtained from a patient will absorb or release oxygen when exposed to an atmosphere having a gas or oxygen content different from that of the blood. For example, the oxygen content of arterial blood is often measured in patients suffering from heart and lung diseases. In order to obtain reliable or accurate test results, it is important to prevent or miminize the exposure of the blood sample to contaminating gas atmospheres during the taking of the sample, storage and transportation to the gas analyzing machine. In U.S. Pat. No. 3,867,923, collection devices are disclosed which have a bag that is normally maintained collapsed until the blood enters and expands the bag. With the collection devices of the above patent, however, the air originally in the needle cannula and internal passageways of the devices remains with the sample of blood, and oxygen in such air can be absorbed by the blood. While air could be expelled from the bag after it is filled by compressing the bag with the needle pointing upwardly, such removal of air would tend to result in the undesirable issuance of some blood from the needle. Also, since the air is in contact with the blood during the time it takes to fill the bag, some absorption of oxygen occurs.

SUMMARY OF THE INVENTION

It is therefore an object of the present invention to provide an improved blood sampling device useful in collecting samples for gas analysis wherein the above disadvantages are substantially obviated.

Another object of the present invention is to provide a blood collection device which minimizes or substantially obviates absorption of atmospheric gas into the blood.

Another object is to provide a blood collection device which is especially useful for blood-gas analysis and which is efficient in operation and relatively inexpensive so that it can be of the "disposable" or single-use type.

In accordance with one aspect of the present invention, a blood collection device is provided which includes a flexible, normally collapsed container, and a support having means for supporting a needle cannula. The support has a passage for connecting a needle cannula in fluid communication with a collection chamber of the container. A gas vent connects with the passage for venting gas to the atmosphere. The inlet to the container can be manually closed to permit gas or air normally within the needle cannula and passage to escape through the vent. In accordance with another aspect of the present invention, the container has a gas insolating chamber which connects with the collection chamber to permit movement of gas from the collection chamber to the insolating chamber.

These, as well as other objects and advantages of the present invention, will become apparent from the following detailed description and accompanying drawing.

BRIEF DESCRIPTION OF THE DRAWING

FIG. 1 is a perspective view of a blood collection device in accordance with the preferred embodiment of the invention and shown with a needle cannula attached thereto;

FIG. 2 is a fragmentary perspective view of the collection device of FIG. 1 but with a closure cap attached thereto instead of the cannula;

FIG. 3 is an elevational plan view of the container of the collection device of FIG. 1;

FIG. 4 is an elevational plan view of the bottom member of the container shown in FIG. 1;

FIG. 5 is an enlarged cross-sectional view taken along the line 5—5 of FIG. 2;

FIG. 6 is a cross-sectional view taken along the line 6—6 of FIG. 5;

FIG. 7 is a side view of the support member of FIG. 5; and

FIG. 8 is a fragmentary sectional view illustrating a closure cap of modified construction.

DESCRIPTION OF THE PREFERRED EMBODIMENT

Referring now to the drawing and particularly to FIG. 1, a blood sampling or collection device 10 is provided with a needle cannula 12 for collecting a blood sample that can be subsequently used in a gas analyzing machine for measuring the amount of gas, such as carbon dioxide or oxygen, present in the blood. The blood collection device 10 includes a flexible, normally collapsed, blood collection bag or container 14 connected to a relatively rigid support member 16. The support 16 has a luer tapered male connector 17 adapted to receive the hub of needle 12 which has a female luer connection or a closure cap 18 as seen in FIG. 2.

The container 14, as also seen in FIG. 3, includes elongate upper and lower flat, flexible sheet members 20 and 22 that provide opposed side walls of the container. The wall members of the container are preferably formed of a transparent plastic material such as a film of acrylonitrile-methyl acrylate copolymer, or a polyester. The material should preferably be one of low gas permeability. Members 20 and 22 lie in face-to-face contact with each other throughout their entire facing surface areas so that no air is present between these surface areas. The two container members are similar except that the lower member 22, as best seen in FIG. 4, is provided with an opening 24 that serves as the blood inlet to the container, opening 24 being the only opening to the container 14. The facing marginal surfaces about the complete periphery of the members are secured together such as by a conventional heat-forming process. The heat-sealed portions of the members are indicated at 26 in FIG. 3.

In their normal empty condition shown in the figures of the drawing, the container members 20 and 22 are in flat facing contact with each other providing a main blood collection chamber 28 and gas or air isolating chamber 30 at the proximal end of the bag 14. The chamber 30 has an entrance passage of restricted size indicated at 32 in FIG. 3 and is formed between the proximal ends of heat-sealing extensions or portions 26' and 26". These sealing extensions extend angularly from the marginal sealing portions 26 toward each other and define, with portions 26, the air isolating chamber 30.

The supporting member 16 includes an elongate flat portion 34 integrally connected to a generally triangular enlarged end portion 36 at the distal end of the member having an inclined wall or ramp 38 extending from the flat portion 34 to the distal end of the support. The Luer connector 17 is integrally connected to enlarged end 36 at the distal end of the support and is in fluid communication with a passage 40 formed in the enlarged end of the support. Passage 40 extends longitudinally parallel to the flat portion 34 and flat bottom of the support and connects with an opening 42 formed in the inclined wall portion 38 of the support. Support 16 is also provided with a gas vent passage 44 that is shown extending normally to passage 40 from the side of the support to the opening 42, as best seen in FIGS. 2, 5 and 6. A hydrophobic filter 46 is connected across gas vent passage 44 and is shown secured over the outer or external end of the vent passage as seen in FIG. 7. Filter 46 allows gas or air to flow through it to the atmosphere but prevents blood from flowing through it. The filter 46 may be of any conventional hydrophobic filter material that will perform this function. One example of a suitable filter is the "Acropor" 0.8 micron hydrophobic filter sold by the Gelman Company. The support member 16 is preferably molded of a suitable transparent plastic so that blood can be seen through it.

The container 14 has a distal end portion 48 secured to the inclined wall 38 of support 16 such that the opening 24 in the lower member 22 is directly over the opening 42 in the support member. The bottom surface of the lower container member 22 is sealed to the inclined wall 38 in continuous mating surface areas extending entirely around the openings 24 and 42. In this way, fluid cannot flow between the wall 38 and bottom of member 22 and to the atmosphere. Blood flowing into the collection device from passage 40 flows into opening 42, the vent passage 44 and the container 14. The container and support may be secured together such as by a suitable clear cement or solvent. A proximal end portion of the container 14 is also secured to the proximal end portion of the support to hold the container in the position shown in FIG. 1.

Before packaging, the interior of device 10, including the passage 40, opening 42, and interior of container 14, is coated with an anti-coagulant, such as a heparin solution and allowed to dry. This prevents the blood from clotting when put in use. The interior facing walls of chambers 28 and 30 of the container are in direct contact with each other throughout their mating surfaces so that substantially no air exists between them after they are coated and packaged. Preferably, the device 10 is packaged with the cap 18 closing the distal end and accompanying a suitably packaged needle cannula 12.

In use, the cap 18 is removed from the luer connector 17 but not discarded since it can be used subsequently, as will be discussed. The hub of needle 12 is then attached to connector 38 so that the device is in condition to be used, which is the condition shown in FIG. 1. A finger or thumb of the person taking the sample, such as indicated in FIG. 5 at 49, is placed over the area of the upper container member 20 such that facing areas of the upper and lower bag members around the opening 42 are sealingly closed so that no fluid can enter container 14. These internal facing surfaces of the container members about the opening 42 which are squeezed between the thumb or finger and support 16 serve as a manually operable fluid valve connected between the opening 42 and the container chamber 28. With the thumb so positioned and the device 10 oriented so that the filter is on top, the needle 12 is inserted into a blood vessel of the patient, such as in an artery. The blood pressure in the artery causes blood to enter the needle and to force air that is normally in the needle and in all of the passages including passage 40 and passage 44, out through the hydrophobic filter 46 since no fluid can flow into the container 14. Once blood fills the passages including vent passage 44 and has therefore caused the air to be expelled through filter 46, the thumb is removed from the device. Blood in the passages can be seen through the transparent container and support member. The blood pressure causes blood to move through the opening 24 of the container and to flow between the upper and lower members 20 and 22 causing them to separate and effect expansion of the container 14. The blood enters the blood collection chamber 28, and when a sufficient amount of blood has flowed into the collection chamber, the needle 12 is removed from the patient. The needle 12 is removed from connector 17 and cap 18 is returned to the connector to sealingly close the distal end of passage 40.

In the event of an error in technique, such as the raising of the thumb to open the valve and collection chamber 28 before all of the original internal air of the device has been expelled through the filter 46, air or air bubbles in collection chamber 28 can be moved to the air isolation chamber 30. For example, should air bubbles appear in the chamber 28, the container 14 can be manipulated by the fingers in a manner to move the bubbles proximally in the container through the passage 32 and into the isolating chamber 30. The angular sealing portion 26' and 26" (FIG. 3) aid in pushing air or bubbles toward the isolating chamber. The container walls at the passage 32 will tend to return to a contact engagement condition after fluid has been forced through the passage so as to maintain the passage closed after all gas has been moved to the isolating chamber 30.

The device 10 containing the blood can then be transported to a blood-gas analysis machine. For example, in some cases, the cap can be removed and the device 10 placed into an inlet tube of the machine such that the tube enters the passage 40 and passes through opening 24 and into chamber 30. The tube of the machine readily enters the collection chamber because the longitudinal axis of the passage intersects the inlet 24. The blood can then be moved from the container into the machine.

The blood-gas analysis machine can then provide a substantially accurate indication of the gas content of the blood actually in the patient since substantially little or no oxygen was absorbed by the blood during the above blood collecting procedures.

Since the blood collection device 10 can be economically formed of plastic materials, it can be disposed of after a single use, and the advantages of avoiding sterilization of parts at the point of use can be avoided.

The closure cap 18 is constructed so as to prevent the introduction of air into the passage 40 when it is applied to the blood filled device. As seen in FIG. 5, the cap 18 has a central integral, tapered plug portion 50 within a cylindrical guide portion 52, which is inserted into the distal end of passage 40 to frictionally hold it on the device and to provide the closure seal for the device. Since there are spaces between the inner surface of the guide 52 and outer luer taper surface of connector 17, no air is forced into the passage 40.

In FIG. 8, a closure cap 54 of modified construction is shown. Cap 54 has a cylindrical guide 56 which frictionally surrounds the connector 17 to hold it in place.

An air vent passage 58 extending axially through the cap and a hydrophobic filter 60, disposed across the vent passage, allows air or gas that otherwise might be trapped by placement of a cap onto the device, to escape through the filter to the atmosphere.

The container 14, in some cases, may be used in a collection device that does not have means for venting air to the atmosphere. In such a device, air that flows into the collection chamber 28 can be moved into the isolating chamber 30 immediately after obtaining the sample in order to reduce the amount of absorption of oxygen into the blood.

Instead of heat-sealing the opposed sheet members, 20 and 22 of the container 14, they may be cemented together by a suitable adhesive or solvent.

The dry coating of anti-coagulant on the interior portions of the container makes it unnecessary to employ an anti-coagulant at the point of use.

It will not be apparent that blood collection devices made in accordance with the present invention greatly minimize absorption of gas or oxygen into the blood sample so that highly accurate gas measurements are obtainable.

As various changes could be made in the above construction without departing from the scope of the invention, it is intended that all matter contained in the above description or shown in the accompanying drawing shall be interpreted as illustrative and not in a limiting sense.

What is claimed is:

1. A blood collection device comprising a support member having fluid passage means therein and including means for supporting a needle cannula in fluid communication with said passage means, an opening in said support member connecting with said passage means, a vent passage connected between said passage means and the atmosphere to allow gas to flow from said passage means to the atmosphere, and a collapsible container connected to said support member and including a collection chamber having an inlet connected to said opening and being expansible in response to the flow of blood into said collection chamber, said collection chamber having opposed side walls normally in face-to-face contact with each other so that substantially no air is in said collection chamber, a gas isolation chamber, and an entrance passage connecting said collection chamber with said isolation chamber for manually moving any gas from said collection chamber to said isolation chamber.

2. The device of claim 1 wherein said inlet is at the distal end portion of said collection chamber and said isolating chamber is at the proximal end portion of said collection chamber.

3. The device of claim 1 further including other means for allowing gas to pass from said vent passage to the atmosphere but preventing blood flow therethrough.

4. The device of claim 3 wherein said other means comprises a hydrophobic filter connected across said vent passage.

5. The device of claim 1 wherein said container comprises a pair of flat sheet members of flexible plastic material sealed together along a predetermined path in flat face-to-face contact relation to form said collection chamber.

6. The device of claim 5 wherein said sheet members are sealed together along another predetermined path to provide said gas isolating chamber with an entrance passage connecting said chambers together.

7. The device of claim 6 wherein at least portions of said support member and said sheet members are substantially transparent to enable viewing of blood in said passage means and said collection chamber.

8. The device of claim 1 wherein said container inlet is disposed over said opening in said support member so that pressure applied to the exterior of said container in areas surrounding said container inlet and said opening closes said container preventing the ingress of fluid therein.

9. The device of claim 8 wherein said support member is an elongate member of relatively rigid plastic material having a flat portion, and a distal end portion connected to said flat portion and said cannula supporting means and having said passage means and said opening therein, said container comprises a pair of elongate substantially flexible plastic sheet members connected together in flat face-to-face contact with each other to form a blood collection chamber therebetween and with the major portion of said container supported by said flat portion of said support member.

10. The device of claim 9 wherein said sheet members are further connected together along a predetermined path to form said air isolating chamber.

11. The device of claim 6 wherein said predetermined paths include a pair of portions extending proximally and inclined toward each other, said pair of portions being closely spaced from each other at their proximal ends to provide said entrance.

12. The device of claim 11 wherein said container inlet is an opening in one of said sheet members.

13. The device of claim 1 wherein said cannula supporting means comprises a luer tapered connection means for sealingly receiving a luer tapered connector of a needle cannula.

14. The device of claim 13 further including a closure cap, and wherein said passage means extends through said connection means, said cap is connectable to said connection means to sealingly close said passage means from the atmosphere.

15. The device of claim 14 wherein said cap includes a plug member insertable into said passage means, and air passage means between the connector means and cap means to prevent ingress of air into said passage means when said plug is inserted into said passage means to close the same.

16. The device of claim 14 wherein said cap has an axial opening therethrough for the passage of air therethrough when said cap is connected to said connection means, and a hydrophobic filter connected across said axial opening to allow air to pass through said cap but prevent blood from flowing therethrough.

17. A blood collection device comprising a support member having passage means therein and including means for supporting a needle cannula in fluid communication with said passage means, and a collapsible container connected to said support member and including a collection chamber having opposed side walls normally in face-to-face contact with each other so that substantially no air is in said collection chamber, an inlet connecting said passage means with said collection chamber, a gas isolation chamber, and an entrance passage connecting said collection chamber with said isolation chamber for allowing movement of air from said collection chamber to said isolating chamber by manipulating said container.

18. The device of claim 17 wherein said container comprises a pair of flexible, flat sheet members of plastic material sealed together along a predetermined path to define said collection and gas isolating chambers.

19. The device of claim 18 wherein said gas isolating chamber is disposed proximally of said collection chamber, one of said sheet members being connected to said support member, the other of said sheet members being substantially transparent.

20. The device of claim 19 wherein said predetermined path includes a pair of portions extending angularly toward each other with their adjacent ends closely spaced from each other to separate said collection chamber from said gas isolating chamber, said entrance passage being formed between said adjacent ends.

21. The device of claim 17 wherein said support member has a vent passage therein connected with said passage means and communicating with the atmosphere, and a hydrophobic filter across said vent passage to allow gas to escape from the passage means to the atmosphere, said inlet being manually closeable from the exterior of the device.

22. The device of claim 1 wherein said passage means and the interior of said container have a dry coating of an anti-coagulant thereon.

23. The device of claim 17 wherein said passage means is substantially straight and extends from the distal end of said support member to said opening whereby a straight tube of a blood-gas analysis machine can be inserted into said passage from the distal end thereof and enter said collection chamber for removing a sample of blood therefrom.

24. The device of claim 17 wherein the width of said entrance passage is substantially less than the width of said collection chamber, and said collection chamber narrows toward said entrance passage to facilitate movement of any air from the collection chamber to said isolation chamber after blood is introduced into said collection chamber.

25. The device of claim 17 wherein said isolation chamber and entrance passage have opposed walls in face-to-face contact.

26. The device of claim 17 wherein said container comprises a pair of upper and lower sheet members sealed together along predetermined paths to define said collection chamber, said entrance passage, and said isolation chamber, the opposed walls of said entrance passage are normally in face-to-face contact normally closing said entrance passage, and said opposed walls of said entrance passage being movable apart when said container is manipulated to move fluid from said collection chamber to said isolation chamber.

27. A blood collection device for receiving a sample of blood from a blood source comprising a support member having fluid passage means therein including means at the distal end portion thereof for supporting a needle cannula in fluid communication with said passage means, said support member having an opening therein connected to the proximal end portion of said passage means, a vent passage connected to said passage means and normally communicating with the atmosphere, a hydrophobic filter connected across said vent passage for allowing air to pass from said passage means to the atmosphere but preventing blood flow therethrough, and an expansible blood collection container including upper and lower flexible sheet members normally disposed in face-to-face contact with each other so that there is normally substantially no air between facing portions of said container, said container having an inlet connected to allow the flow of blood from said passage means and through said opening to said container, said upper sheet member having a portion covering said opening whereby a manually applied downward pressure on said portion of said upper sheet member prevents fluid flow into said container so that air initially in said passage means flows through said vent passage and said filter to the atmosphere when blood initially flows into said passage means from said blood source, and removal of said applied pressure allows blood thereafter to flow through said inlet into said container substantially free of air.

28. A method of collecting a sample of blood from a blood source comprising the steps of providing the device of claim 27, supporting a needle cannula on said passage means, manually applying a pressure on said portion of said upper sheet member to prevent fluid flow into said container, while applying the pressure positioning the free end of said cannula in a source of blood, maintaining said pressure until substantially all of the air normally initially in said cannula, passage means, and vent passage has been forced by the blood through said filter to the atmosphere and then removing said pressure to allow blood to flow into said container.

* * * * *